United States Patent
Yoshimura et al.

(10) Patent No.: US 12,031,239 B2
(45) Date of Patent: Jul. 9, 2024

(54) ACRYLIC FIBER FOR ARTIFICIAL HAIR, METHOD FOR MANUFACTURING SAID FIBER, AND HEADDRESS PRODUCT CONTAINING SAID FIBER

(71) Applicant: KANEKA CORPORATION, Osaka (JP)

(72) Inventors: Satoru Yoshimura, Hyogo (JP); Masaru Anahara, Hyogo (JP); Hiroki Shinomiya, Hyogo (JP); Masanobu Tamura, Hyogo (JP); Ryohei Noishiki, Hyogo (JP); Aki Kano, Hyogo (JP); Akihiro Okamoto, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 271 days.

(21) Appl. No.: 17/152,916

(22) Filed: Jan. 20, 2021

(65) Prior Publication Data

US 2021/0140071 A1    May 13, 2021

Related U.S. Application Data

(60) Division of application No. 15/856,937, filed on Dec. 28, 2017, now abandoned, which is a continuation of
(Continued)

(51) Int. Cl.
| | |
|---|---|
| *D01F 6/40* | (2006.01) |
| *A41G 3/00* | (2006.01) |
| *A41G 5/00* | (2006.01) |
| *A61L 27/16* | (2006.01) |
| *D01D 1/02* | (2006.01) |
| *D01D 5/06* | (2006.01) |

(52) U.S. Cl.
CPC ............. *D01F 6/40* (2013.01); *A41G 3/00* (2013.01); *A41G 5/0006* (2013.01); *A41G 5/004* (2013.01); *A61L 27/16* (2013.01); *D01D 1/02* (2013.01); *D01D 5/06* (2013.01); *A41G 3/0083* (2013.01); *D10B 2321/101* (2013.01); *D10B 2503/08* (2013.01)

(58) Field of Classification Search
CPC ... D01F 6/40; D01D 5/06; D01D 1/02; A41G 5/0006; A41G 5/004; D10B 2321/101; D10B 2503/08
USPC ........................................................ 428/364
See application file for complete search history.

(56) References Cited

U.S. PATENT DOCUMENTS

| | | | | |
|---|---|---|---|---|
| 3,862,070 A | * | 1/1975 | Fukushima | C08K 3/22 524/424 |
| 7,531,600 B1 | * | 5/2009 | Rey | C08F 2/32 210/698 |

(Continued)

*Primary Examiner* — Lynda Salvatore
(74) *Attorney, Agent, or Firm* — Osha Bergman Watanabe & Burton LLP (57) ABSTRACT

An acrylic fiber for artificial hair includes an acrylic copolymer obtained by copolymerizing acrylonitrile, vinyl chloride and/or vinylidene chloride, and a sulfonic acid group-containing vinyl monomer; and an organic solvent that can dissolve the acrylic copolymer, where the organic solvent is present in an amount of 0.1 to 3% by mass with respect to the total mass of the acrylic fiber for artificial hair. The acrylic fiber for artificial hair has an average surface roughness of 5900 μm² or less in an area of 40 μm long and 80 μm wide of the side surface of the fiber.

8 Claims, 4 Drawing Sheets

Related U.S. Application Data application No. PCT/JP2016/069053, filed on Jun. 27, 2016.

(56) References Cited

U.S. PATENT DOCUMENTS

| | | | |
|---|---|---|---|
| 2003/0154564 A1* | 8/2003 | Nakashima | D06P 1/928 8/408 |
| 2004/0074509 A1* | 4/2004 | Murata | D01F 6/40 132/201 |

* cited by examiner

ACRYLIC FIBER FOR ARTIFICIAL HAIR, METHOD FOR MANUFACTURING SAID FIBER, AND HEADDRESS PRODUCT CONTAINING SAID FIBER

This application is a divisional filed pursuant to 35 U.S.C. § 121 of U.S. patent application Ser. No. 15/856,937, filed Dec. 28, 2017, which is a continuation of PCT/JP2016/069053, filed on Jun. 27, 2016. The contents of the priority applications are incorporated by reference in their entirety.

TECHNICAL FIELD

One or more embodiments of the present invention relate to acrylic fibers for artificial hair that have good curl setting properties with hot water and good hackling properties. One or more embodiments of the present invention also relate to a method for producing the acrylic fibers for artificial hair, and hair ornament products including the acrylic fibers for artificial hair.

BACKGROUND

Conventionally, acrylic fibers have been used as fibers for artificial hair because their texture, gloss, and voluminousness are quite similar to those of human hair. For example, Patent Document 1 proposes artificial hair that uses fibers composed of an acrylic copolymer containing 35 to 75% by mass of acrylonitrile, 25 to 65% by mass of a halogen-containing vinyl monomer such as vinyl chloride, and 0 to 10% by mass of a vinyl monomer copolymerizable with the acrylonitrile and the halogen-containing vinyl monomer. Patent Document 2 proposes artificial hair that uses fibers composed of an acrylic copolymer containing 35 to 75% by mass of acrylonitrile, 25 to 65% by mass of vinyl chloride and/or vinylidene chloride, and 0 to 10% by mass of a vinyl monomer copolymerizable with the acrylonitrile and the vinyl chloride and/or the vinylidene chloride. Patent Document 3 proposes synthetic fibers for artificial hair that are composed of an acrylic copolymer containing 30 to 80% by mass of acrylonitrile and 20 to 70% by mass of vinyl chloride and/or vinylidene chloride.

PRIOR ART DOCUMENTS

Patent Documents

Patent Document 1: JP 2002-227018 A
Patent Document 2: JP 2002-227028 A
Patent Document 3: WO 2012/043348

However, when the acrylic copolymer formed by copolymerizing acrylonitrile and vinyl chloride and/or vinylidene chloride, as disclosed in Patent Documents 1 to 3, is dissolved in an organic solvent such as dimethyl sulfoxide to prepare a spinning solution, and acrylic fibers are produced by wet spinning the spinning solution, such acrylic fibers have poor curl setting properties with hot water.

In the fibers for artificial hair, a hackling machine is generally used to open the fibers. Therefore, the fibers have been required to improve their hackling properties.

One or more embodiments of the present invention provide acrylic fibers for artificial hair that have good curl setting properties with hot water and good hackling properties. One or more embodiments of the present invention also provide a method for producing the acrylic fibers for artificial hair, and hair ornament products including the acrylic fibers for artificial hair.

SUMMARY

One or more embodiments of the present invention relate to an acrylic fiber for artificial hair that includes an acrylic copolymer obtained by copolymerizing acrylonitrile, vinyl chloride and/or vinylidene chloride, and a sulfonic acid group-containing vinyl monomer. The acrylic fiber for artificial hair includes an organic solvent that can dissolve the acrylic copolymer in an amount of 0.1 to 3% by mass with respect to the total mass of the acrylic fiber for artificial hair. The acrylic fiber for artificial hair has an average surface roughness of 5900 $\mu m^2$ or less in an area of 40 $\mu m$ long and 80 $\mu m$ wide of the side surface of the fiber.

One or more embodiments of the present invention also relate to a method for producing an acrylic fiber for artificial hair. The method includes: preparing a spinning solution in which an acrylic copolymer obtained by copolymerizing acrylonitrile, vinyl chloride and/or vinylidene chloride, and a sulfonic acid group-containing vinyl monomer is dissolved in an organic solvent; and wet spinning the spinning solution to form an acrylic fiber. The spinning solution contains 8 to 16 parts by mass of water with respect to 100 parts by mass of the acrylic copolymer. In the wet spinning, a content of the organic solvent that can dissolve the acrylic copolymer in the acrylic fiber is adjusted to 0.1 to 3% by mass.

One or more embodiments of the present invention also relate to a hair ornament product including the acrylic fiber for artificial hair.

One or more embodiments of the present invention can provide acrylic fibers for artificial hair that have good curl setting properties with hot water and good hackling properties. One or more embodiments of the present invention can also provide hair ornament products including the acrylic fibers for artificial hair. Moreover, the production method of one or more embodiments of the present invention can provide acrylic fibers for artificial hair that have good curl setting properties with hot water and good hackling properties.

DETAILED DESCRIPTION OF THE EMBODIMENTS

The inventors of the present disclosure have found that acrylic fibers that include an acrylic copolymer obtained by copolymerizing acrylonitrile, vinyl chloride and/or vinylidene chloride, and a sulfonic acid group-containing vinyl monomer exhibit improved curl setting properties with hot water by incorporating a predetermined amount of an organic solvent that can dissolve the acrylic copolymer. Moreover, the inventors of the present disclosure have also found that the acrylic fibers exhibit better hackling properties by adjusting the surface roughness on the side surface of the fibers to a predetermined value.

The acrylic copolymer may contain 30 to 70% by mass of acrylonitrile, 25 to 69.5% by mass of vinyl chloride and/or vinylidene chloride, and 0.5 to 5% by mass of a sulfonic acid group-containing vinyl monomer with respect to the total mass of the acrylic copolymer. In other words, the acrylic copolymer is obtained by polymerizing a total of 100% by mass of a monomer mixture containing 30 to 70% by mass of acrylonitrile, 25 to 69.5% by mass of vinyl chloride and/or vinylidene chloride, and 0.5 to 5% by mass of a sulfonic acid group-containing vinyl monomer. When the content of acrylonitrile in the acrylic copolymer is 30 to 70% by mass, the heat resistance is improved. Therefore, the acrylic fibers including this acrylic copolymer can be curled with a hair iron by appropriately setting the processing temperature. When the content of vinyl chloride and/or vinylidene chloride in the acrylic copolymer is 25 to 69.5% by mass, the flame resistance is improved. When the acrylic copolymer contains 0.5 to 5% by mass of a sulfonic acid group-containing vinyl monomer, the dye affinity is improved and the hydrophilicity is increased, resulting in a low void fraction. The acrylic copolymer may contain 1% by mass or more of a sulfonic acid group-containing vinyl monomer, or 1.5% by mass or more of a sulfonic acid group-containing vinyl monomer with respect to the total mass of the acrylic copolymer. Moreover, the acrylic copolymer may contain 69% by mass or less of vinyl chloride and/or vinylidene chloride, or 68.5% by mass or less of vinyl chloride and/or vinylidene chloride with respect to the total mass of the acrylic copolymer.

The acrylic copolymer may contain vinyl chloride from the viewpoint of excellent texture.

The sulfonic acid group-containing vinyl monomer is not particularly limited. Examples of the sulfonic acid group-containing vinyl monomer include sulfonic acid compounds such as allylsulfonic acid, methallylsulfonic acid, styrenesulfonic acid, isoprenesulfonic acid, and 2-acrylamido-2-methylpropanesulfonic acid, metal salts (e.g., sodium salts) of the sulfonic acid compounds such as sodium p-styrenesulfonate, and amine salts of the sulfonic acid compounds such as styrenesulfonic acid amine salt. These sulfonic acid group-containing vinyl monomers may be used individually or in combination of two or more.

The acrylic copolymer can be prepared by copolymerizing acrylonitrile, vinyl chloride and/or vinylidene chloride, and a sulfonic acid group-containing vinyl monomer. The copolymerization method is not particularly limited, and may be a general vinyl polymerization method such as a slurry polymerization method, an emulsion polymerization method, or a solution polymerization method. Among them, the emulsion polymerization method may be used from the viewpoint of ease of preparation of the polymer having a desired molecular weight. Moreover, the polymerization may be continuously performed in a single reaction vessel from the viewpoint of the stability of the production process.

When acrylonitrile, vinyl chloride and/or vinylidene chloride, and a sulfonic acid group-containing vinyl monomer are continuously polymerized in a single reaction vessel to form an acrylic copolymer, the introduction of the sulfonic acid group-containing vinyl monomer into the reaction vessel may be performed in the following manner. The sulfonic acid group-containing vinyl monomer is not introduced into the reaction vessel at the beginning of the polymerization reaction, but introduced into the reaction vessel at a predetermined time after the start of the polymerization reaction when the yield of the acrylic copolymer reaches 8 to 21% by mass of the intended amount of the acrylic copolymer, and then continues to be introduced at a constant rate until the end of the polymerization reaction. The acrylic copolymer thus obtained is dissolved in an organic solvent to prepare a spinning solution. Wet spinning of the spinning solution can easily provide fibers with a smooth surface.

The emulsion polymerization can be performed in the same manner as a usual method using an emulsifier in the presence of an aqueous initiator, except that the introduction of the sulfonic acid group-containing vinyl monomer into the reaction vessel is performed as described above.

The aqueous initiator is not particularly limited, and may be persulfate that functions as an oxidizing agent. This is because the activation energy is low, and the yield can be improved even at a low temperature. The persulfate may be added in an amount of 0.1 to 0.4 parts by weight, or in an amount of 0.2 to 0.3 parts by weight with respect to 100 parts by weight of the total weight of the monomers.

Examples of the persulfate include ammonium persulfate and potassium persulfate, but the persulfate is not limited thereto. Examples of a reducing agent include sodium hydrogen sulfite, sodium hydrogen bisulfite, and sulfurous acid, but the reducing agent is not limited thereto. In addition, a catalytic decomposition accelerator such as iron sulfate or copper sulfate and a chain transfer agent such as t-butyl mercaptan or 2-mercaptoethanol may be used. The emulsifier may be an anionic surfactant that is generally used in the emulsion polymerization, and may be, e.g., alkyl benzene sulfonate or alkyl alcohol sulfate salt. However, the emulsifier is not limited to these examples. The alkyl alcohol sulfate salt may be, e.g., sodium lauryl sulfate.

From the viewpoint of the productivity and quality of the acrylic copolymer, the polymerization temperature may be 40 to 70° C., or 45 to 55° C. When materials such as monomers, an initiator, an emulsifier, and water are continuously added to the reaction vessel, they should be added with precision under the control of a metering pump. However, those materials may be previously cooled as needed in order to ensure the removal of the heat of polymerization generated in the reaction vessel. The latex may be discharged from the reaction vessel in the following manner. Using a metering pump or a flow control valve, the latex may be discharged from the bottom or the lower portion of the side of the reaction vessel, so that the copolymer solution in the same amount as that of the added materials is discharged while maintaining the pressure inside the reaction vessel. The average residence time in the reaction vessel (i.e., the time obtained by dividing the capacity of the reaction vessel by the amount of materials added per hour) may be generally 0.5 to 10 hours, or 1.5 to 3 hours in view of the mechanical stability of the latex and the quality of fibers made of the copolymer. If necessary, a polymerization inhibitor, a coagulant, a flame retardant, or a pH adjuster may be added to the acrylic copolymer latex discharged from the reaction vessel. Moreover, unreacted monomers may be recovered or post-polymerized. Then, the latex can be formed into the acrylic copolymer by known methods such as coagulation, heat treatment, dehydration, water washing, and drying.

In the acrylic fibers for artificial hair, the content of the organic solvent that can dissolve the acrylic copolymer (also referred to as an "organic solvent A" in the following) is 0.1 to 3% by mass. When the content of the organic solvent A in the acrylic fibers is within the above range, both the curl setting properties with hot water and the spinnability are improved. On the other hand, if the content of the organic solvent A in the acrylic fibers is less than 0.1% by mass, it is not possible to improve the curl setting properties with hot water. If the content of the organic solvent A in the acrylic fibers is more than 3% by mass, the curl retention properties may be degraded, and a single yarn breakage may occur due to poor spinnability. The content of the organic solvent A in the acrylic fibers may be 0.2% by mass or more, or 0.25% by mass or more, or 0.3% by mass or more. In this case, the content of the organic solvent A in the acrylic fibers may be 2.8% by mass or less, or 2.5% by mass or less, or 2% by mass or less. In one or more embodiments of the present invention, 20 parts by mass of a predetermined organic solvent is added to 100 parts by mass of the acrylic copolymer, and then heated at 90° C. for 30 minutes. At this time, if the resulting solution is transparent, the organic solvent is defined as "an organic solvent that can dissolve the acrylic copolymer." Examples of the organic solvent that can dissolve the acrylic copolymer include acetonitrile, acetone, dimethyl sulfoxide, N,N-dimethylformamide, dimethylacetamide, dimethyl sulfone, ε-caprolactam, ethylene carbonate, and sulfolane. In one or more embodiments, when the acrylic fibers for artificial hair as described herein include two or more types of organic solvents A, the content of the organic solvents A represents the total content of the two or more types of organic solvents A. In one or more embodiments of the present invention, the solvent A has the function of improving the curl setting properties of the acrylic fibers with hot water. Therefore, the content of the solvent A in the fibers may be 0.1 to 3% by mass before heat setting or the like. The content of the solvent A in the fibers may be 0.1 to 3% by mass or less than 0.1% by mass after heat setting or the like.

From the viewpoint of ensuring good texture and good combing properties, the acrylic fibers for artificial hair may include, but are not limited to, at least one selected from the group consisting of dimethyl sulfoxide, N,N-dimethylformamide, dimethylacetamide, dimethyl sulfone, ε-caprolactam, ethylene carbonate, and sulfolane as the organic solvent A. From the viewpoint of preventing the evaporation of the organic solvent in the drying process, the acrylic fibers for artificial hair may include at least one selected from the group consisting of dimethyl sulfoxide, N,N-dimethylformamide, dimethylacetamide, dimethyl sulfone, ε-caprolactam, ethylene carbonate, and sulfolane as the organic solvent A. From the viewpoint of safety for the human body, the acrylic fibers for artificial hair may include at least one selected from the group consisting of dimethyl sulfoxide, dimethyl sulfone, ε-caprolactam, ethylene carbonate, and sulfolane as the organic solvent A. It is also envisioned that the acrylic fibers for artificial hair may include at least one selected from the group consisting of dimethyl sulfone, ε-caprolactam, ethylene carbonate, and sulfolane as the organic solvent A.

In one or more embodiments of the present invention, when the boiling point of the organic solvent A is higher than that of water, the content of the organic solvent A in the acrylic fibers for artificial hair is measured and calculated as follows. A glass sample bottle containing pure water is prepared, in which fibers are placed so that the water will not overflow. Then, the fibers are heated in hot water at 95° C. or more for 2 hours or more to extract the organic solvent in the fibers. The extract is analyzed by, e.g., gas chromatography, and the mass (W1) of the organic solvent in the fibers is determined. The fibers in the glass sample bottle are washed with pure water, and then dried at 110° C. for 4 hours or more. Thus, the mass (W2) of the dried fibers is measured. Using the following formula, the content of the organic solvent A in the acrylic fibers is calculated:

Content of organic solvent $A$ in acrylic fiber (% by mass)=$(W1)/(W1+W2)\times100$.

In one or more embodiments of the present invention, when the boiling point of the organic solvent A is lower than that of water, the content of the organic solvent A in the acrylic fibers for artificial hair is measured and calculated as follows. Fibers are dissolved in an organic solvent that can dissolve the acrylic copolymer (but is different from the organic solvent in the fibers) to form a polymer solution. The polymer solution is analyzed by gas chromatography, and the mass (W3) of the organic solvent in the fibers is determined. Fibers with the same mass as that of the fibers dissolved in the organic solvent are dried at 110° C. for 4 hours or more. Thus, the mass (W4) of the dried fibers is measured. Using the following formula, the content of the organic solvent A in the acrylic fibers is calculated:

Content of organic solvent $A$ in acrylic fiber (% by mass)=$(W3)/(W4)\times100$.

The average surface roughness of the acrylic fibers for artificial hair may be 5900 $\mu m^2$ or less, or 5600 $\mu m^2$ or less, or 5200 $\mu m^2$ or less in an area of 40 μm long and 80 μm wide of the side surface of the fibers. From the viewpoint of excellent hackling properties, the maximum surface roughness of the acrylic fibers for artificial hair may be 6800 $\mu m^2$ or less, or 6500 $\mu m^2$ or less, or 6200 $\mu m^2$ or less in an area of 40 μm long and 80 μm wide of the side surface of the fibers. In one or more embodiments of the present invention, the surface roughness is measured and calculated in the manner as will be described later.

From the viewpoint of excellent hackling properties, the void fraction of the acrylic fibers for artificial hair may be 60% or less, or 45% or less, or 40% or less. In one or more embodiments of the present invention, the void fraction is measured and calculated in the manner as will be described later.

The acrylic fibers for artificial hair may have an apparent glass transition temperature (also referred to as apparent Tg) of 90° C. or less, or 89° C. or less, or 88° C. or less. When the apparent Tg of the fibers is within the above range, the curl setting properties with hot water can be improved, even if the temperature of the hot water is low, e.g., at 60 to 70° C. In one or more embodiments of the present invention, the apparent Tg of the fibers means a peak temperature of tan δ. The peak temperature of tan δ is a temperature at which dynamic viscoelasticity (tan δ) reaches the maximum value. The dynamic viscoelasticity (tan δ) is calculated by the following formula: Dynamic viscoelasticity (tan δ)=Loss modulus (E")/Storage modulus (E'), where the loss modulus (E") and the storage modulus (E') of the fibers are measured in accordance with JIS K 7244 by a thermal analysis measuring device.

The single fiber fineness of the acrylic fibers for artificial hair may be 10 to 100 dtex, or 20 to 95 dtex, or 30 to 90 dtex from the viewpoint of making the fibers suitable for artificial hair. In this specification, the single fiber fineness means the average fineness of 100 randomly selected filaments.

The acrylic fibers for artificial hair can be produced in the following manner. An acrylic copolymer is obtained by copolymerizing acrylonitrile, vinyl chloride and/or vinylidene chloride, and a sulfonic acid group-containing vinyl monomer. The acrylic copolymer is dissolved in an organic solvent, to which water is added in an amount of 8 to 16 parts by mass with respect to 100 parts by mass of the acrylic copolymer, thereby forming a spinning solution. Then, the spinning solution is wet spun so that the content of the organic solvent that can dissolve the acrylic copolymer in the acrylic fibers is adjusted to 0.1 to 3% by mass.

Examples of the organic solvent that can dissolve the acrylic copolymer, which is used for the spinning solution, include acetone, dimethyl sulfoxide, N,N-dimethylformamide, and dimethylacetamide. From the viewpoint of productivity, the organic solvent may be at least one selected from the group consisting of dimethyl sulfoxide, N,N-dimethylformamide, and dimethylacetamide. From the viewpoint of productivity and safety, the organic solvent may be dimethyl sulfoxide.

The spinning solution contains 8 to 16 parts by mass of water with respect to 100 parts by mass of the acrylic copolymer. If the amount of water added to the spinning solution is less than 8 parts by mass with respect to 100 parts by mass of the acrylic copolymer, the acrylic fibers obtained by wet spinning of this spinning solution will have a high void fraction, so that the hackling properties may be degraded. On the other hand, if the amount of water added to the spinning solution is more than 16 parts by mass with respect to 100 parts by mass of the acrylic copolymer, the acrylic fibers obtained by wet spinning of this spinning solution will have a rough surface, so that the hackling properties may be degraded. From the viewpoint of reducing the void fraction and the surface roughness, the spinning solution may contain 8 to 15 parts by mass of water, or 8 to 14 parts by mass of water, or 8 to 13 parts by mass of water with respect to 100 parts by mass of the acrylic copolymer.

The spinning solution may contain polyphosphate from the viewpoint of effectively suppressing the coloring of the acrylic fibers. The content of the polyphosphate may be 0.05 parts by mass or more, or 0.06 parts by mass or more, or 0.07 parts by mass or more with respect to 100 parts by mass of the acrylic copolymer. From the viewpoint of color protection and spinnability, the upper limit of the polyphosphate may be 5 parts by mass or less, or 4 parts by mass or less, or 3 parts by mass or less, or 2 parts by mass or less, or 1 part by mass or less with respect to 100 parts by mass of the acrylic copolymer.

The polyphosphate is not particularly limited, and may be inorganic polyphosphate. Examples of the inorganic polyphosphate include pyrophosphate, tripolyphosphate, tetrapolyphosphate, trimetaphosphate, and tetrametaphosphate. In particular, tripolyphosphate may be used from the viewpoint of ease of availability and high solubility. The type of salt is not particularly limited, and may be, e.g., sodium salt, potassium salt, or ammonium salt. Among them, water-soluble salts such as sodium salt and potassium salt may be used from the viewpoint of their excellent solubility in water. The pyrophosphate (also referred to as diphosphate) may be, e.g., sodium pyrophosphate or potassium pyrophosphate. The tripolyphosphate may be, e.g., sodium tripolyphosphate, aluminum dihydrogentripolyphosphate, or potassium tripolyphosphate. The tetrapolyphosphate may be, e.g., sodium tetrapolyphosphate or potassium tetrapolyphosphate.

Although depending on the composition of the acrylic copolymer, the spinning solution may contain, e.g., 20 to 30% by mass of the acrylic copolymer, 65.2 to 78.49% by mass of the organic solvent, 1.5 to 4.8% by mass of water, and 0.01 to 1.5% by mass of the polyphosphate with respect to the total mass of the spinning solution. The spinning solution may contain 22 to 30% by mass of the acrylic copolymer, 66 to 75.99% by mass of the organic solvent, 2 to 4% by mass of water, and 0.01 to 1.5% by mass of the polyphosphate with respect to the total mass of the spinning solution. The spinning solution may further contain 25 to 30% by mass of the acrylic copolymer, 65 to 72.99% by mass of the organic solvent, 2 to 3.5% by mass of water, and 0.01 to 1.5% by mass of the polyphosphate with respect to the total mass of the spinning solution.

The spinning solution may also contain other additives as needed to modify the fiber characteristics unless they interfere with the effects of one or more embodiments of the present invention. Examples of the additives include gloss control agents such as titanium dioxide, silicon dioxide, and esters and ethers of cellulose derivatives including cellulose acetate, coloring agents such as organic pigments, inorganic pigments, and dyes, and stabilizers for improving light resistance and/or heat resistance.

The spinning solution can be prepared by forming a slurry of the acrylic copolymer containing the acrylic copolymer, water, and the organic solvent that can dissolve the acrylic copolymer, and supplying the slurry of the acrylic copolymer to a thin film evaporator, where water in the slurry is evaporated. The slurry of the acrylic copolymer may contain polyphosphate. The above method allows a wet resin to be used as the acrylic copolymer for the preparation of the spinning solution. Moreover, water in the slurry of the acrylic copolymer (containing the acrylic copolymer, water, and the organic solvent) is evaporated by the thin film evaporator, so that the acrylic copolymer can be dissolved in the organic solvent, and the spinning solution can be stably and efficiently provided that contains 8 to 16 parts by mass of water with respect to 100 parts by mass of the acrylic copolymer. In one or more embodiments of the present invention, unless otherwise noted, the acrylic copolymer is in a dry state and does not contain water.

Figure 1:
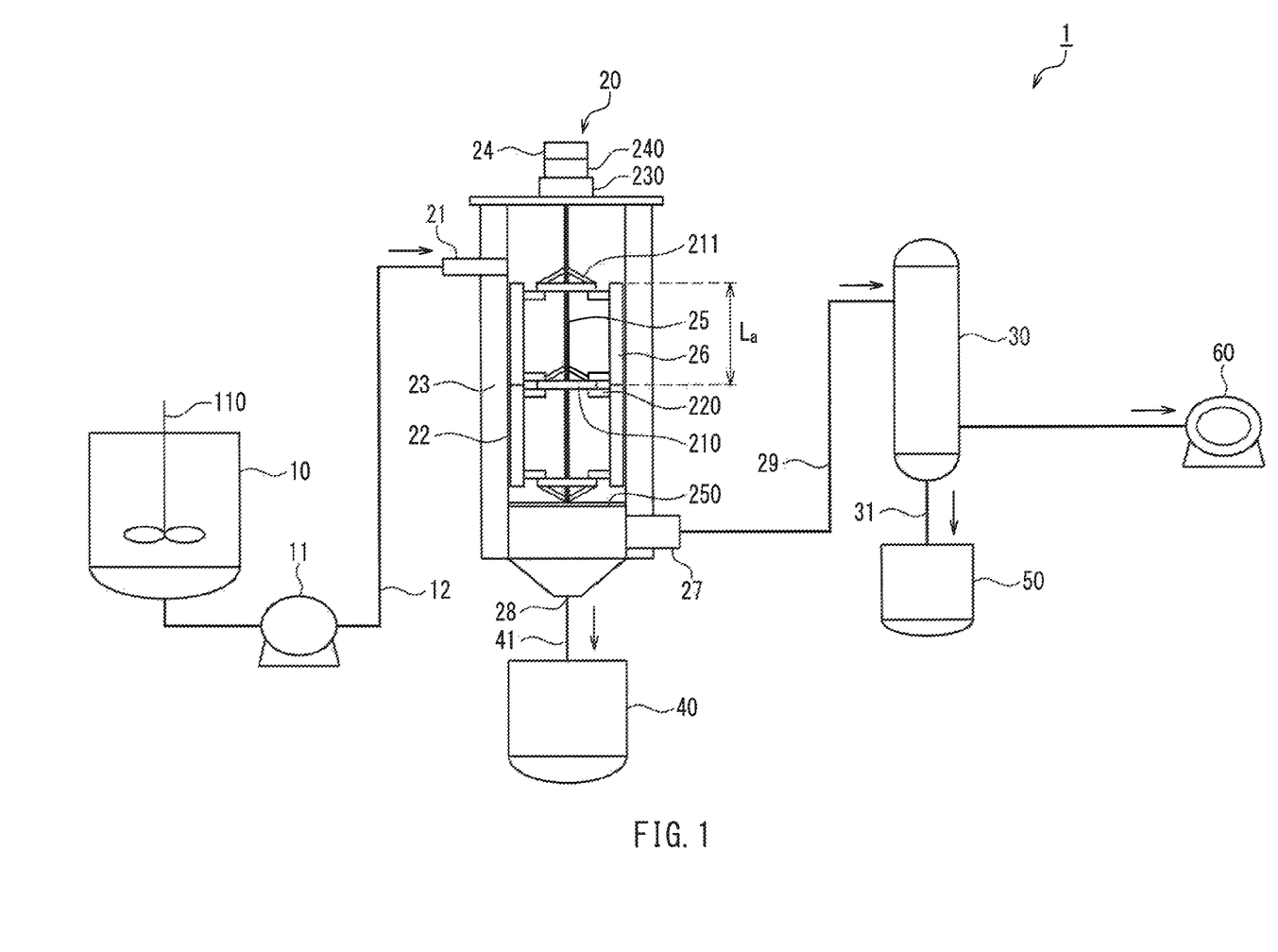
FIG. 1 is a schematic diagram of an example of a production apparatus for producing a spinning solution according to one or more embodiments of the present invention.

The spinning solution can be prepared by, e.g., a production apparatus as illustrated in FIG. 1. FIG. 1 is a schematic view of an example of a production apparatus for producing the spinning solution. As illustrated in FIG. 1, the production apparatus 1 includes a feed tank 10, a thin film evaporator 20, a condenser 30, a bottom recovery tank 40, a condensate recovery tank 50, and a vacuum pump 60.

The feed tank 10 may include an agitator 110. In the feed tank 10, a slurry of the acrylic copolymer (also referred to as a feed slurry in the following), containing the acrylic copolymer, water, and the organic solvent, is stirred by the agitator 110. Then, the slurry is supplied to the thin film evaporator 20 through a conduit 12 having a liquid feed pump 11.

Figure 2:
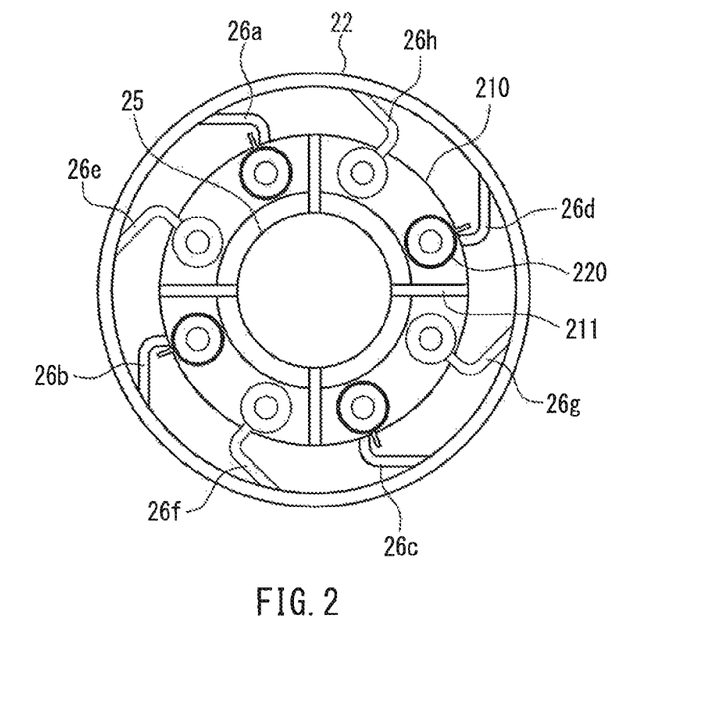
FIG. 2 is a schematic cross-sectional view for explaining the arrangement of movable blades in a thin film evaporator, where four movable blades are arranged in an upper stage and four movable blades are arranged in a lower stage so that the movable blades in the upper stage are displaced 45 degrees from the adjacent movable blades in the lower stage.

The thin film evaporator 20 includes a feed inlet 21, a heat transfer body 22, a jacket 23, a motor 24, a rotation axis 25, movable blades 26, a vaporized component outlet 27, and a bottom outlet 28. The feed slurry is introduced from the feed inlet 21 and repeatedly diffused over the inner wall surface of the heat transfer body 22 by the movable blades 26. As a result, water contained in the feed slurry is evaporated. In this case, water may be evaporated, since the organic solvent contained in the feed slurry has a higher boiling point than water. The vaporized component is drawn by the suction of the vacuum pump 60 and transferred to the condenser 30 via the vaporized component outlet 27 and a conduit 29. In the condenser 30, the vaporized component is cooled and condensed. The condensate is collected in the condensate recovery tank 50 via a conduit 31. The residue (i.e., the spinning solution in which water or the like has been evaporated) is collected as a bottom flow into the bottom recovery tank 40 via the bottom outlet 28 and a conduit 41. The movable blades 26 are connected to blade support rings 210 by movable blade holders 220. The blade support rings 210 are fixed to the rotation axis 25 by support ring fixtures 211. Accordingly, the movable blades 26 are coupled to the rotation axis 25 via the blade support rings 210. The method for coupling the movable blades to the rotation axis is not particularly limited. The movable blades 26 swing in the circumferential direction in accordance with the rotation of the rotation axis 25. The rotation axis 25 is rotatably supported by a mechanical seal 230, an upper bearing 240, and a lower bearing 250. The motor 24 controls the rotation of the rotation axis 25. A heating medium such as vapor is circulated in the jacket 23 to adjust the temperature of the inner wall surface or the inside of the heat transfer body 22.

From the viewpoint of productivity, the amount of the slurry of the acrylic copolymer supplied to the thin film evaporator may be 50 kg/hr·m$^2$ or more, or 100 kg/hr·m$^2$ or more, or 150 kg/hr·m$^2$ or more, or 200 kg/hr·m$^2$ or more. In one or more embodiments of the present invention, the amount of the slurry of the acrylic copolymer supplied to the thin film evaporator is defined by the following formula based on the supply rate of the slurry of the acrylic copolymer per hour and the heat transfer area of the thin film evaporator.

Amount of slurry of acrylic copolymer supplied to thin film evaporator (kg/hr·m$^2$)=Supply rate of slurry of acrylic copolymer per hour (kg/hr)/ Heat transfer area of thin film evaporator (m$^2$)

Figure 4A:
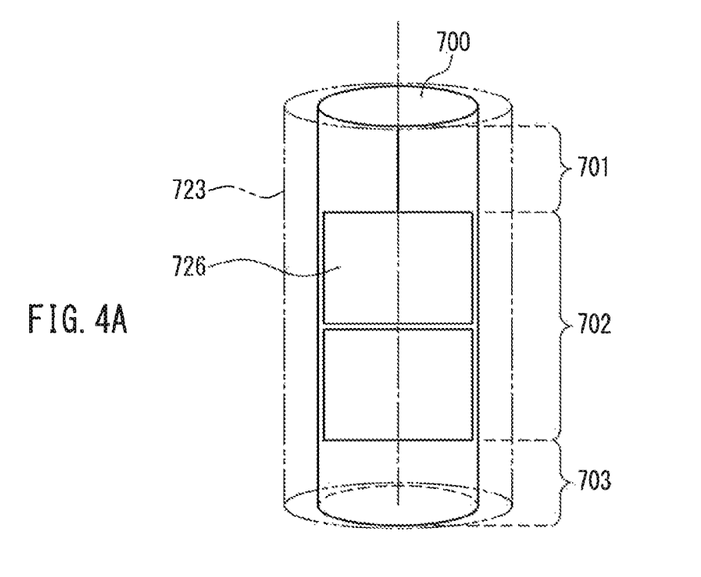
FIGS. 4A and 4B are schematic diagrams of a heat transfer area of a thin film evaporator according to one or more embodiments of the present invention.
Figure 4B:
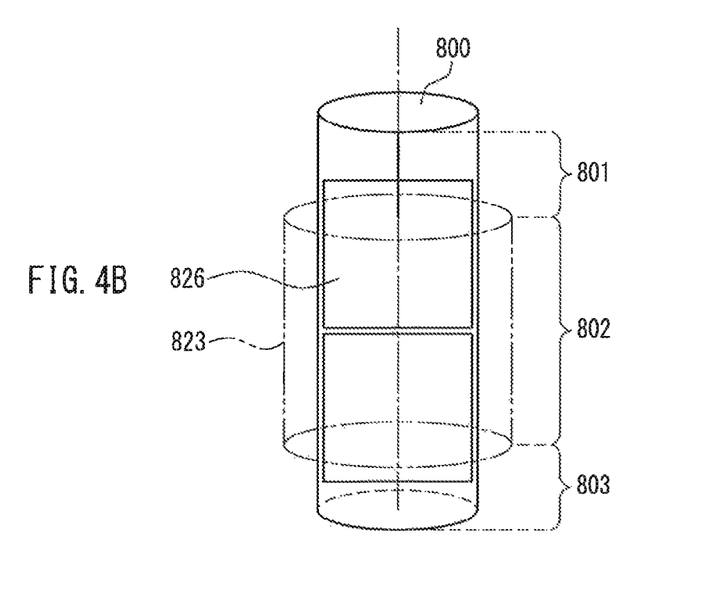

In one or more embodiments of the present invention, the heat transfer body of the thin film evaporator has a portion on the inner wall surface that is to be heated and brought into contact with the movable blades. The heat transfer area of the thin film evaporator means the surface area of this portion. When the portion is heated and brought into contact with the movable blades, evaporation proceeds while a thin film is being formed. In one or more embodiments of the present invention, the heat transfer area of the thin film evaporator may be 50% or more of the total surface area of the inner wall surface of the heat transfer body. For example, as illustrated in FIG. 4A, a heat transfer body 700 of a thin film evaporator has a thin film formation and evaporation portion 702 on the inner wall surface. The thin film formation and evaporation portion 702 is heated by a heating medium such as vapor circulating in a jacket 723 and is brought into contact with movable blades 726, so that evaporation proceeds while a thin film is being formed. Thus, the surface area of the thin film formation and evaporation portion 702 is the heat transfer area of the above thin film evaporator. In the thin film evaporator of FIG. 4A, the length of the movable blades is smaller than that of the jacket. Therefore, there are portions 701 and 703 on the inner wall surface of the heat transfer body 700 where no thin film is formed because the portions 701 and 703 are heated by a heating medium such as vapor circulating in the jacket 723, but will not be brought into contact with the movable blades. FIG. 4B illustrates another example in which the length of the movable blades is larger than that of the jacket. In this case, a heat transfer body 800 of a thin film evaporator has a thin film formation and evaporation portion 802 on the inner wall surface. The thin film formation and evaporation portion 802 is heated by a heating medium such as vapor circulating in a jacket 823 and is brought into contact with movable blades 826, so that evaporation proceeds while a thin film is being formed. Thus, the surface area of the thin film formation and evaporation portion 802 is the heat transfer area of the above thin film evaporator. There are portions 801 and 803 on the inner wall surface of the heat transfer body 800 where evaporation does not proceed because the portions 801 and 803 are not heated. For clarification purposes, the movable blades are spaced from the inner wall surface of the heat transfer body in FIGS. 4A and 4B. Actually, however, the tips of the movable blades are in contact with the inner wall surface of the heat transfer body. The material of the heat transfer body is not particularly limited, and may be any material that has thermal conductivity. Examples of the material include stainless steel (also referred to as "SUS"), carbon steel, glass with its inner wall surface being lined, and Hastelloy. The heat transfer body may be made of either one type of material or two or more types of materials The centrifugal force per 100 mm axial length of a movable blade is 0.1 N or more, or 0.14 N or more, or 0.2 N or more with respect to the unit amount (1 kg/hr·m$^2$) of the slurry of the acrylic copolymer supplied to the thin film evaporator. This can improve the treatment efficiency of the thin film evaporator for the feed slurry, which results in high productivity.

Figure 5A:
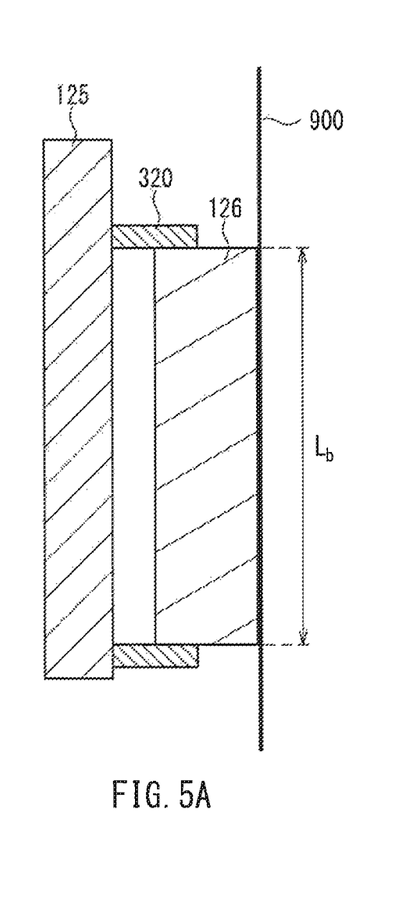
FIGS. 5A to 5C are schematic diagrams of the axial lengths of movable blades of different shapes according to one or more embodiments of the present invention.
Figure 5B:
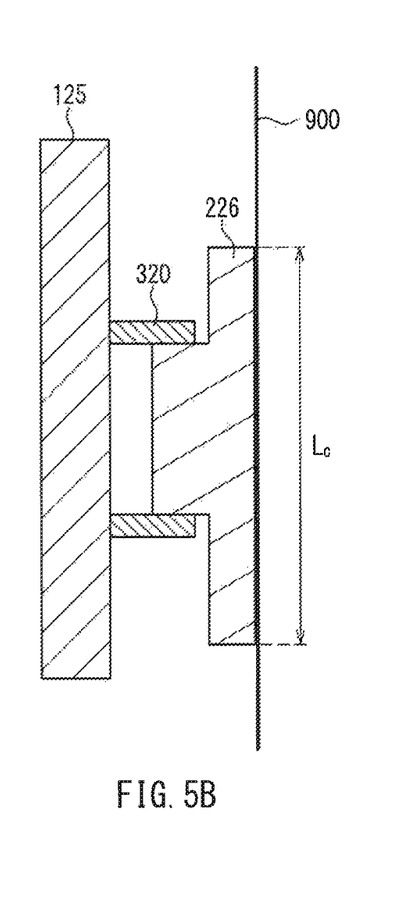
Figure 5C:
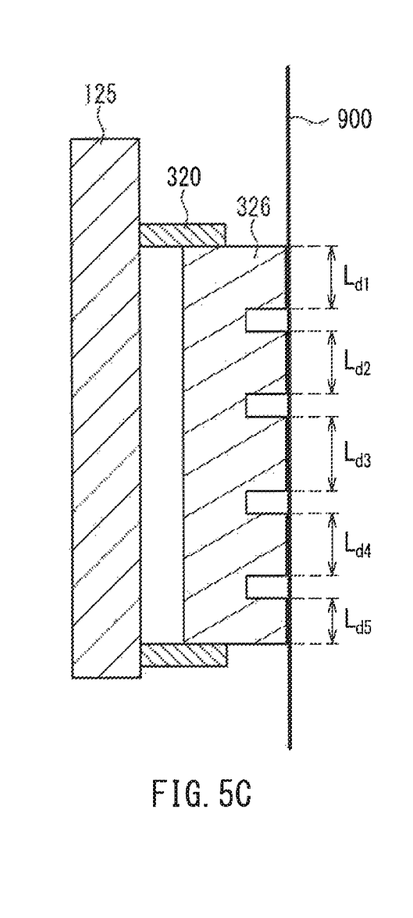

In one or more embodiments of the present invention, the axial length of a movable blade means the axial length of the tip of the movable blade that comes into contact with the inner wall surface of the heat transfer body of the thin film evaporator. FIGS. 5A-5C show schematic diagrams of the axial length of movable blades of different shapes. FIGS. 5A and 5B illustrate movable blades having no notch in their tips. As illustrated in FIG. 5A, a movable blade 126 has no notch in the tip. The movable blade 126 is provided with movable blade holders 320 and coupled to a rotation axis 125. In this case, the axial length of the movable blade is represented by $L_b$, which is the axial length of the tip of the movable blade 126 that comes into contact with an inner wall surface 900 of a heat transfer body of a thin film evaporator. As illustrated in FIG. 5B, a movable blade 226 has no notch in the tip. The movable blade 226 is provided with the movable blade holders 320 and coupled to the rotation axis 125. In this case, the axial length of the movable blade is represented by $L_c$, which is the axial length of the tip of the movable blade 226 that comes into contact with the inner wall surface 900 of the heat transfer body of the thin film evaporator. FIG. 5C illustrates a movable blade having notches in its tip. As illustrated in FIG. 5C, a movable blade 326 has notches in the tip. The movable blade 326 is provided with the movable blade holders 320 and coupled to the rotation axis 125. In this case, the axial length of the movable blade is represented by the total of $L_{d1}$, $L_{d2}$, $L_{d3}$, $L_{d4}$, and $L_{d5}$, each of which is the axial length of the tip of the movable blade 326 that comes into contact with the inner wall surface 900 of the heat transfer body of the thin film evaporator.

In one or more embodiments of the present invention, the centrifugal force per 100 mm axial length of a movable blade is calculated by the following formula.

$$F_{100}=(F/B_L)\times 0.1$$

$$F=M(R/2)\omega^2=M(R/2)(2\pi(N/60))^2, \quad \text{[Formula 1]}$$

where F (N) represents the centrifugal force, M (kg) represents the total mass of movable blades, R (m) represents the inner diameter of a heat transfer body of a thin film evaporator, N (rpm) represents the number of revolutions of a rotation axis, $B_L$ (m) represents the total axial length of movable blades, and $F_{100}$ (N) represents the centrifugal force per 100 mm axial length of a movable blade.

In the above formula, when the thin film evaporator includes one movable blade, the total mass of movable blades (M: kg) means the mass of one movable blade. When the thin film evaporator includes two or more movable blades, it means the total mass of two or more movable blades. In one or more embodiments of the present invention, the mass of one movable blade means the mass of the movable blade that affects the centrifugal force, and includes the mass of members such as the movable blade holders that hold the movable blade and move together with the movable blade. In the above formula, when the thin film evaporator includes one movable blade, the total axial length of movable blades ($B_L$: m) means the axial length of one movable blade. When the thin film evaporator includes two or more movable blades, it means the total axial length of two or more movable blades. The centrifugal force per 100 mm axial length of a movable blade can be adjusted by, e.g., the inner diameter of the heat transfer body of the thin film evaporator, the number of revolutions of the rotation axis, and the mass and length of the movable blade.

The movable blades are arranged symmetrically with respect to the rotation axis of the heat transfer body, which is identified as a symmetry axis, and the feed slurry is uniformly distributed on the inner wall surface of the heat transfer body. The number of movable blades is not particularly limited, and may be appropriately determined in accordance with the length and inner diameter of the heat transfer body. Moreover, depending on the length of the heat transfer body and the axial length of the movable blades, the movable blades may be separately arranged in two or more stages in the longitudinal direction. A plurality of movable blades, e.g., two, four, or six movable blades may be arranged in each stage.

In one or more embodiments of the present invention, a thermal-centrifugal force efficiency index η may be 300 N·cal/kg·° C. or more, or 350 N·cal/kg·° C. or more from the viewpoint of heat transfer. When the thermal-centrifugal force efficiency index η is 300 N·cal/kg·° C. or more, the heat transfer becomes better, and the evaporation efficiency is improved. The thermal-centrifugal force efficiency index η is calculated by the following formula.

$\eta = Fa \times \kappa$ $\kappa = ((t1/\lambda 1) + \ldots + (ti/\lambda i))^{\wedge}(-1)$ $Fa = F_{100}/f,$ [Formula 2]

where $F_{100}$ (N) represents the centrifugal force per 100 mm axial length of a movable blade, f (kg/hr·m²) represents the amount of the slurry of the acrylic copolymer supplied to a thin film evaporator, Fa (N) represents the centrifugal force per 100 mm axial length of a movable blade with respect to the unit amount (1 kg/hr·m²) of the slurry of the acrylic copolymer supplied to the thin film evaporator, λ1 ... λi (kcal/m·hr·° C.) represents a thermal conductivity of each of the materials constituting the heat transfer body of the thin film evaporator, t1 ... ti (m) represents a thickness of each of the materials (walls) constituting the heat transfer body of the thin film evaporator, and η (N·kcal/kg·° C.) represents a thermal-centrifugal force efficiency index.

In one or more embodiments of the present invention, when the heat transfer body is made of one type of material, the thermal-centrifugal force efficiency index q is calculated by the following formula.

$\eta = Fa \times \kappa$ $\kappa = (t1/\lambda 1)^{\wedge}(-1) = \lambda 1/t1$ $Fa = F_{100}/f,$ [Formula 3]

where $F_{100}$ (N) represents the centrifugal force per 100 mm axial length of a movable blade, f (kg/hr·m²) represents the amount of the slurry of the acrylic copolymer supplied to a thin film evaporator, Fa (N) represents the centrifugal force per 100 mm axial length of a movable blade with respect to the unit amount (1 kg/hr·m²) of the slurry of the acrylic copolymer supplied to the thin film evaporator, λ1 (kcal/m·hr·° C.) represents a thermal conductivity of the material of the heat transfer body of the thin film evaporator, t1 (m) represents a thickness of the material (wall) of the heat transfer body of the thin film evaporator, and η (N·kcal/kg·° C.) represents a thermal-centrifugal force efficiency index.

The internal pressure of the thin film evaporator 20 may be under reduced pressure from the viewpoint of promoting the evaporation of water. The internal pressure of the thin film evaporator 20 may be 20 kPa or less, or 5 kPa or less, or 3 kPa or less from the viewpoint of productivity.

In the thin film evaporator, the temperature of the heating steam in the jacket may be 110 to 150° C., or 120 to 140° C. from the viewpoint of facilitating the evaporation of water.

The thin film evaporator may be a commercially available movable blade type thin film evaporator. For example, a centrifugal thin film evaporator manufactured by Hitachi Plant Mechanics Co., Ltd. or a thin film evaporator manufactured by Buss-SMS-Canzler GmbH may be used.

The wet spinning can be performed by the same procedure as that of the general wet spinning except that the content of the organic solvent in the acrylic fibers after the water washing process is adjusted to 0.1 to 3% by mass. The wet spinning includes a coagulation process, a water washing process, and a drying process. The wet spinning may also include a bath drawing process that is to be performed before or after the water washing process. Moreover, the wet spinning may include an oil application process that is to be performed before the drying process. Further, the wet spinning may include a drawing process and a thermal relaxation process that are to be performed after the drying process.

Coagulation Process

For example, first, the spinning solution is extruded through a spinning nozzle or directly into a coagulation bath containing an aqueous solution of the organic solvent, where the extruded spinning solution is coagulated to form filaments. The coagulation bath may contain a mixed solution of water and the organic solvent from the viewpoint of easily controlling the coagulation state. For example, the coagulation bath may contain an aqueous solution of the organic solvent composed of 20 to 75% by mass of the organic solvent and 25 to 80% by mass of water, or may contain an aqueous solution of the organic solvent composed of 30 to 70% by mass of the organic solvent and 30 to 70% by mass of water, or may contain an aqueous solution of the organic solvent composed of 40 to 70% by mass of the organic solvent and 30 to 60% by mass of water with respect to the total mass of the coagulation bath. The temperature of the coagulation bath may be, e.g., 5 to 40° C. If the solvent concentration in the coagulation bath is too low, the coagulation is accelerated, and thus it is likely that a coagulation structure will be rough and voids will be formed inside the fibers.

The organic solvent in the coagulation bath is not particularly limited, and may be a good solvent for the acrylic copolymer. From the viewpoint of productivity, the organic solvent may be at least one selected from the group consisting of dimethyl sulfoxide, dimethylacetamide, and N,N-dimethylformamide. From the viewpoint of safety, the organic solvent may be dimethyl sulfoxide. Moreover, from the viewpoint of the quality of the acrylic fibers and ease of process control, the organic solvent in the spinning solution may be the same as that in the coagulation bath.

Bath Drawing Process

Next, the acrylic fibers (coagulated yarns) may be drawn in a drawing bath. The drawing bath may be a water bath or may contain an aqueous solution of the organic solvent having a lower concentration of the organic solvent than the coagulation bath. The temperature of the drawing bath may be 30° C. or more, or 40° C. or more, or 50° C. or more. The organic solvent in the drawing bath may be the same as that in the coagulation bath. The draw ratio is not particularly limited, and may be 2 to 8 times, or 2 to 7 times, or 2 to 6 times from the viewpoint of improving the fiber strength and the productivity.

Water Washing Process

Next, the acrylic fibers (coagulated yarns or drawn yarns) are washed with water to remove the organic solvent. The water washing process can be performed by immersing the fibers in a water bath containing warm water at 30° C. or more, or an aqueous solution of the organic solvent having a lower concentration of the organic solvent than the coagulation bath. After immersion in the water bath, the fibers may be pressed by a nip roll. In order to remove the organic solvent from the acrylic fibers in a short time without using the water bath, the water washing process may include spraying water on the acrylic fibers and pressing the acrylic fibers sprayed with water by a nip roll.

In one or more embodiments of the present invention, the "nip roll" is not particularly limited, and may be any nip roll that is generally used to produce fibers with a wet spinning method. The "press by a nip roll" means that pressure is applied to the acrylic fibers, e.g., by passing the acrylic fibers between a pair of upper and lower nip rolls or by wrapping the acrylic fibers around a nip roll. The pressure application method is not particularly limited as long as the nip roll can apply pressure to the acrylic fibers. For example, the pressure application method may include applying pressure to the upper nip roll by a cylinder, putting a weight on the upper nip roll, or pulling the upper nip roll downward.

The nip roll may be, e.g., a rubber nip roll or a metal nip roll. The rubber nip roll (also referred to as a rubber roll) is suitable for the upper nip roll. The metal nip roll (also referred to as a metal roll) is suitable for the lower nip roll. The material of the rubber nip roll may be, e.g., natural rubber, styrene-butadiene rubber, nitrile rubber, chloroprene rubber, butyl rubber, ethylene-propylene rubber, chlorosulfonated polyethylene rubber, silicone rubber, fluororubber, or urethane rubber. The rubber nip roll may be formed by wrapping rubber around a metal roll. From the viewpoint of maintaining the cross-sectional shape of the fibers, the thickness of the rubber may be 3 mm or more, or 5 mm or more, or 8 mm or more. The material of the metal nip roll may be, e.g., stainless. The hardness of the nip roll may be 40 to 100, or 50 to 85, or 55 to 80. In one or more embodiments of the present invention, the hardness of the nip roll is measured in accordance with JIS K 6253 by a type A durometer.

In one or more embodiments of the present invention, the acrylic fibers may be alternately sprayed with water and pressed by a nip roll for a plurality of times. Alternatively, the acrylic fibers may be sprayed with water at least two times and then pressed by a nip roll at least one time.

From the viewpoint of improving the removal efficiency of the organic solvent in the acrylic fibers, the water spray and the press by a nip roll may be alternately repeated six times or more, or eight times or more, or ten times or more.

The water washing process can be performed by alternately arranging a nip roll and a water sprayer. When the acrylic fibers are alternately pressed by a nip roll and sprayed with water at least two times, a water washing device can be used that includes two or more sets of nip rolls and water sprayers that are alternately arranged. These nip rolls and water sprayers may be alternately arranged in a single row or multiple rows.

In the water washing process, the water sprayer is not particularly limited, and a nozzle may be used because it is easy to operate. The nozzle can have any shape that is capable of spraying water. For example, the nozzle may be in the form of a slit or a hole. The spray direction is not particularly limited, and water may be sprayed from either side or the bottom. A shower nozzle having a plurality of holes may be used because it can spray water uniformly. The temperature of water to be sprayed is not particularly limited, and may be, e.g., 20 to 95° C. From the viewpoint of improving the desolvation effect to remove the organic solvent, the temperature of water may be 40° C. or more, or 50° C. or more, or 60° C. or more.

From the viewpoint of improving the desolvation effect, the amount of water sprayed (i.e., the spray amount of water) from each nozzle per unit time during the water spray may be 2 times or more, or 3 times or more, or 4 times or more the dry mass of the resin in the acrylic fibers passing through nip rolls per unit time. Moreover, from the viewpoint of reducing the amount of water while improving the desolvation effect, the amount of water sprayed from each nozzle per unit time may be 8 times or less, or 7 times or less, or 6 times or less the dry mass of the resin in the acrylic fibers passing through nip rolls per unit time. The spray amount of water may be constant or different for each nozzle. In the following, the ratio of the amount of water sprayed from each nozzle per unit time to the dry mass of the resin in the acrylic fibers passing through nip rolls per unit time may also be referred to as a water washing ratio.

The dry mass of the resin in the acrylic fibers passing through nip rolls per unit time is calculated by the following formula:

Dry mass of resin in acrylic fiber passing through nip rolls per unit time (g)=(Extrusion amount of spinning solution (L/hr)×Specific gravity of spinning solution (g/L)×(Solid concentration in spinning solution (% by mass))/100, where the solid concentration in the spinning solution (% by mass) is the concentration of the acrylic copolymer in the spinning solution.

The amount of water sprayed from each nozzle per unit time is calculated by the following formula:

Amount of water sprayed from each nozzle per unit time (g)=Dry mass of resin in acrylic fiber passing through nip rolls per unit time (g)×Water washing ratio (times).

From the viewpoint of improving the removal efficiency of the organic solvent in the acrylic fibers, the nip pressure applied by the nip roll may be 0.2 MPa or more, or 0.4 MPa or more, or 0.6 MPa or more. When a plurality of nip rolls is used, the nip pressure may be the same or different among the nip rolls.

The acrylic fibers are not particularly limited, and the ratio of the total fineness to the width of the acrylic fiber bundle may be 300000 dtex/cm or less, or 200000 dtex/cm or less, or 100000 dtex/cm or less from the viewpoint of improving the effect of removing the organic solvent in the water washing process.

Figure 3A:
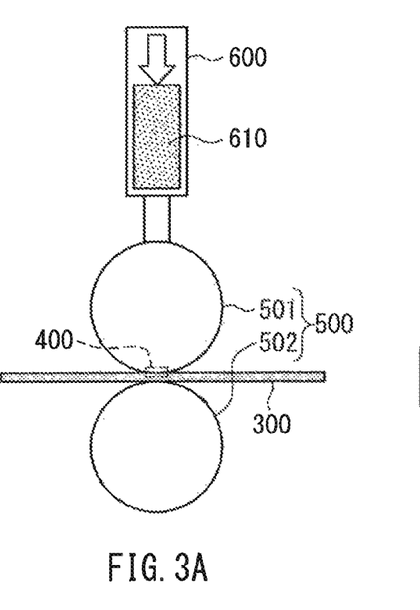
FIG. 3A is a schematic cross-sectional view for explaining the nip pressure applied by nip rolls according to one or more embodiments of the present invention.
Figure 3B:
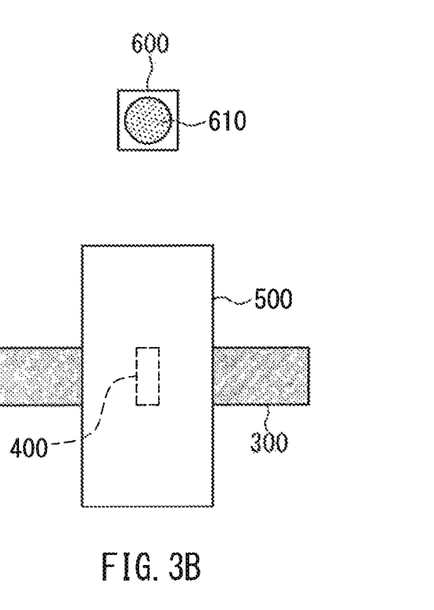
FIG. 3B is a schematic plan view for explaining the nip pressure applied by the nip rolls according to one or more embodiments of the present invention.

In one or more embodiments of the present invention, the nip pressure applied by the nip roll is expressed as follows: the force exerted on a contact portion between the nip roll and the fiber bundle/the area of the contact portion between the nip roll and the fiber bundle. Hereinafter, the nip pressure applied by the nip roll to which pressure is applied by a cylinder will be described with reference to the drawings. FIG. 3A is a schematic cross-sectional view for explaining the nip pressure applied by nip rolls. FIG. 3B is a schematic plan view for explaining the nip pressure applied by the nip rolls. In a cylinder 600 having an inner tube 610, air pressure is applied in the direction indicated by the arrow. When the cylinder 600 applies pressure to an upper nip roll 501, a fiber bundle 300 is pressed between a pair of nip rolls 500 including the upper nip roll 501 and a lower nip roll 502. In this case, reference numeral 400 represents a contact portion between the nip rolls 500 and the fiber bundle 300. When the cross-sectional area of the inner tube 610 of the cylinder 600 is defined as the area of the inner tube of the cylinder, the nip pressure applied by the nip rolls is calculated by the following formula:

Nip pressure=(Air pressure applied to cylinder×Area of inner tube of cylinder)/Area of contact portion between nip roll and fiber bundle.

When a water bath is used in the water washing process, the content of the organic solvent A in the acrylic fibers after the water washing process can be adjusted by the conditions such as the temperature of the water bath. Moreover, when the water spray and the press by a nip roll are alternately performed, the content of the organic solvent A in the acrylic fibers after the water washing process can be adjusted by the conditions such as the nip pressure and the spray amount of water.

The washed acrylic fibers may be impregnated with the organic solvent A. In this case, the fibers have been swelled by water washing, and therefore are easily impregnated with the solvent A. From the viewpoint of simplification of the operation and ease of adjustment of the degree of impregnation with the organic solvent A, the washed acrylic fibers may be impregnated with the organic solvent A at the same time as the application of oil to the acrylic fibers in the oil application process, as it will be described later. The impregnation is not particularly limited, and may be performed, e.g., by spraying a mixture of the organic solvent A and the oil onto the washed acrylic fibers, or by immersing the washed acrylic fibers in the mixture of the organic solvent A and the oil. The content of the organic solvent A in the acrylic fibers can be adjusted by appropriately selecting the impregnation method or the mixing ratio of the organic solvent A in the mixture of the organic solvent A and the oil.

Oil Application Process

Oil may be applied to the acrylic fibers before the acrylic fibers are dried after the water washing process. The oil may be generally used to prevent static electricity, to prevent the adhesion between fibers, or to improve the texture of fibers in the production of the fibers. Any known oil can be used for these purposes. Examples of such oil include the following: anionic surfactants such as phosphates and sulfates; cationic surfactants such as quaternary ammonium salts and imidazolium salts; nonionic surfactants such as ethylene oxide adducts and/or propylene oxide adducts of fats and oils, and polyhydric alcohol partial esters; animal and vegetable fats and oils, mineral oils, and fatty acid esters; and silicone-based surfactants such as amino-modified silicones. These oils may be used individually or in combination of two or more.

From the viewpoint of the stability of oil particles and the adjustment of the optimum solvent content by mixing the organic solvent with the oil, the mixture of the organic solvent A and the oil may contain 0.1 to 10 parts by mass of the organic solvent A, or 0.2 to 5 parts by mass of the organic solvent A, or 0.3 to 2 parts by mass of the organic solvent A with respect to 100 parts by mass of the oil. In this case, the oil may also be an oil solution that is a mixed solution of the oil and water.

From the viewpoint of further improving the curl setting properties with hot water, the organic solvent A that is impregnated into the acrylic fibers in the oil application process may be at least one selected from the group consisting of dimethyl sulfone, ε-caprolactam, ethylene carbonate, and sulfolane, or at least one selected from the group consisting of dimethyl sulfone, ethylene carbonate, and sulfolane, or at least one selected from the group consisting of dimethyl sulfone and ethylene carbonate.

Drying Process

After the oil application process, the acrylic fibers are dried to remove water almost completely in the drying process. The drying method is not particularly limited as long as water can be removed from the fibers. For example, the acrylic fibers may be dried by hot air drying or by contact with a heating roller. The drying temperature is not particularly limited, and may be, e.g., 110 to 190° C., or 110 to 170° C.

Drawing Process

Next, the dried fibers may further be drawn as needed. The drawing temperature is not particularly limited, and may be, e.g., 110 to 190° C., or 110 to 160° C. The draw ratio is not particularly limited, and may be, e.g., 1 to 4 times. The total draw ratio, including the bath drawing before the drying process, may be 2 to 12 times.

Thermal Relaxation Process

The fibers that have been dried or that have been dried and then drawn may be relaxed in the thermal relaxation process. The relaxation rate is not particularly limited, and may be, e.g., 5% or more, or 10% or more. The thermal relaxation treatment may be performed in a dry heat atmosphere or a superheated steam atmosphere at a high temperature, e.g., at 130 to 200° C., or at 140 to 190° C. Alternatively, the thermal relaxation treatment may be performed in a pressurized steam atmosphere or a heated and pressurized steam atmosphere at 120 to 180° C. under 0.05 to 0.4 MPa, or under 0.1 to 0.4 MPa.

The acrylic fibers for artificial hair have good curl setting properties with hot water (also simply referred to as "HWS properties" in the following) and good hackling properties. The HWS properties and the hackling properties can be evaluated, e.g., in the manner as described below.

The acrylic fibers for artificial hair can be used to produce hair ornament products. Since the acrylic fibers for artificial hair have good curl setting properties with hot water and good hackling properties, the hair ornament products using the acrylic fibers for artificial hair are also excellent in both the curl setting properties with hot water and the hackling properties. The hair ornament products may include other fibers for artificial hair in addition to the above acrylic fibers. The other fibers for artificial hair are not particularly limited, and may be, e.g., polyvinyl chloride fibers, nylon fibers, polyester fibers, or regenerated collagen fibers.

The hair ornament products may include, e.g., fiber bundles for hair, hair weaves, wigs, braids, toupee, hair extensions, and hair accessories.

EXAMPLES

Hereinafter, one or more embodiments of the present invention will be described in more detail by way of examples. However, the present invention is not limited to the following examples. Unless otherwise noted, the term "part" means "part by mass" and "%" means "% by mass" in the following description.

Example 1

Production Example 1 of Acrylic Copolymer

First, 162.1 parts of ion-exchanged water, 0.87 parts of sodium lauryl sulfate as an emulsifier, 0.06 parts of sodium hydrogen bisulfite, 0.0039 parts of ferrous sulfate heptahydrate, 0.3 parts of sulfuric acid, 3.0 parts of acrylonitrile, and 53.8 parts of vinyl chloride were placed in a 14 L reaction vessel, and the temperature in the reaction vessel was increased to 49° C. Then, a polymerization reaction was started by the addition of 0.01 parts of ammonium persulfate. Subsequently, 41.2 parts of acrylonitrile and 0.263 parts of ammonium persulfate were each added to the reaction vessel continuously at a constant rate for 5 hours and 40 minutes. After 30 minutes from the start of the polymerization reaction, i.e., at the time the yield of the acrylic copolymer reached 9.0% of the intended amount, 2.0 parts of sodium styrenesulfonate was added to the reaction vessel continuously at a constant rate for 5 hours and 10 minutes. The polymerization reaction was performed for a total of 5 hours and 40 minutes. After completion of the polymerization reaction, the residual monomers were removed, thereby providing an acrylic copolymer latex. The acrylic copolymer latex was subjected to salting-out and coagulation, heat treatment, filtration, water washing, and dehydration, so that a wet resin with a water content of 90% was obtained. The water content is defined as the ratio of the mass of water to the mass of a dry resin when the resin is dried at 60° C. for 10 hours. The elemental analysis of the dry resin (obtained by drying the resin at 60° C. for 10 hours) showed that the content of acrylonitrile was 46%. The sulfur analysis of the dry resin showed that the content of sodium styrenesulfonate was 2%. Thus, the resulting acrylic copolymer contained 46.0% of acrylonitrile, 52.0% of vinyl chloride, and 2.0% of sodium para-styrenesulfonate.

Preparation of Spinning Solution

First, the acrylic copolymer (i.e., the wet resin with a water content of 90%) obtained in Production Example 1, an aqueous solution of 0.61% sodium tripolyphosphate, and dimethyl sulfoxide were mixed and stirred to form a slurry of the acrylic copolymer containing 19% of the acrylic copolymer, 22.1% of water (containing 0.61% of tripolyphosphoric acid), and 58.9% of dimethyl sulfoxide. Next, using the apparatus illustrated in FIG. 1, water was evaporated from the slurry of the acrylic copolymer. FIG. 2 illustrates the arrangement of movable blades in a thin film evaporator. Four movable blades 26a, 26b, 26c, and 26d were arranged at regular intervals in the upper stage, and four movable blades 26e, 26f, 26g, and 26h were arranged at regular intervals in the lower stage. The movable blades in the upper stage were displaced 45 degrees from the adjacent movable blades in the lower stage. The inner diameter of the heat transfer body of the thin film evaporator 20 was 0.155 m. The axial length La of a movable blade was 240 mm. The heat transfer area of the heat transfer body was 0.2 m$^2$. The heat transfer body was composed of SUS 304 with a thermal conductivity of 14 kcal/m·hr·° C. The thickness of the wall (composed of SUS 304) of the heat transfer body was 0.004 m. The operating conditions of the thin film evaporator were set such that the number of revolutions was 515 rpm, the circumferential speed was 4.2 m/s, the centrifugal force per 100 mm axial length of a movable blade was 41.3 N, the pressure was 3 kPa, the inlet heating steam temperature was 114.7° C., and the outlet heating steam temperature was 113.5° C. The amount of the slurry of the acrylic copolymer supplied to the thin film evaporator was 275.85 kg/hr·m$^2$. The centrifugal force per 100 mm axial length of a movable blade was 0.150 N with respect to the unit amount (1 kg/hr·m$^2$) of the slurry of the acrylic copolymer supplied to the thin film evaporator. The thermal-centrifugal force efficiency index q was 524.3 N·cal/kg·° C. The spinning solution thus prepared contained the acrylic copolymer with a solid concentration of 28.0%, 0.02135% of tripolyphosphoric acid, and 3.5% of water with respect to 100% of the spinning solution. The spinning solution contained 12.5 parts of water with respect to 100 parts of the acrylic copolymer.

Wet Spinning

The above spinning solution was extruded through a spinning nozzle (pore diameter: 0.3 mm, the number of pores: 1250) into a coagulation bath containing an aqueous solution of DMSO with a concentration of 62% by mass at 20° C., where the extruded spinning solution was coagulated to form filaments. Then, the filaments were drawn to 3 times their original length in a drawing bath containing an aqueous solution of DMSO with a concentration of 50% by mass at 80° C. The ratio of the total fineness to the width of the fiber bundle of the acrylic fibers (drawn yarns) thus obtained was 60000 dtex/cm. The drawn yarns were then introduced into a water washing device. The water washing device included 13 pairs of nip rolls (each having a diameter of 100 mm and a width of 85 mm) and 12 shower nozzles for spraying water in a fan-like pattern. Each pair of nip rolls included an upper rubber roll and a lower metal roll. The upper rubber roll had a hardness of 60 and was formed by wrapping nitrile rubber (NBR) with a thickness of 6 mm around a stainless roll. The lower metal roll was made of SUS 304. In the water washing device, the pairs of nip rolls and the shower nozzles were alternately arranged, and pressure was applied by a cylinder while the drawn yarns passed between the rubber roll and the metal roll, so that the drawn yarns were alternately pressed by the nip rolls and sprayed with water by the shower nozzle. All the shower nozzles sprayed hot water at 80° C. The nip pressure applied by each of the nip rolls due to the cylinder was 0.96 MPa. The residence time for water washing was 14.4 seconds. The amount of water sprayed (i.e., the spray amount of water) from each shower nozzle per unit time was set to 6 times the dry mass of the resin in the acrylic fibers passing through nip rolls per unit time. After the water washing process, the acrylic fibers were immersed in an oil bath (60° C.) for 3 to 5 seconds. The oil bath contained a mixture of 100 parts by mass of oil (including a fatty acid ester oil and a polyoxyethylene surfactant) and 0.5 parts by mass of dimethyl sulfone. Thus, the acrylic fibers were impregnated with the mixture of oil and dimethyl sulfone. Thereafter, the acrylic fibers were dried at 140° C. and drawn to 2 times. The resulting fibers were subjected to a 20% relaxation treatment at 160° C. to provide acrylic fibers having a single fiber fineness of about 46 dtex.

Example 2

Preparation of Spinning Solution

Using the acrylic copolymer containing 46.0% of acrylonitrile, 52.0% of vinyl chloride, and 2.0% of sodium para-styrenesulfonate, which was obtained in Production Example 1, a spinning solution was prepared in the same manner as Example 1 except that the operating conditions of the thin film evaporator were set such that the number of revolutions was 642 rpm, the circumferential speed was 5.2 m/s, the centrifugal force per 100 mm axial length of a movable blade was 48.2 N, the pressure was 2.7 kPa, the inlet heating steam temperature was 129.8° C., and the outlet heating steam temperature was 129.2° C., and the amount of the slurry of the acrylic copolymer supplied to the thin film evaporator was 280.8 kg/hr·m². In this example, the centrifugal force per 100 mm axial length of a movable blade was 0.172 N with respect to the unit amount (1 kg/hr·m²) of the slurry of the acrylic copolymer supplied to the thin film evaporator. The thermal-centrifugal force efficiency index η was 600.3 N·cal/kg·° C. The spinning solution thus prepared contained the acrylic copolymer with a solid concentration of 28.0%, 0.02135% of tripolyphosphoric acid, and 2.24% of water with respect to 100% of the spinning solution. The spinning solution contained 8 parts of water with respect to 100 parts of the acrylic copolymer.

Wet Spinning

Using the above spinning solution, wet spinning was performed in the same manner as Example 1 to provide acrylic fibers having a single fiber fineness of about 46 dtex.

Example 3

Wet spinning was performed in the same manner as Example 1 except that the fibers were washed in a water bath at 90° C. and the oil bath contained a mixture of 100 parts of oil and 1.0 part of ethylene carbonate. Thus, acrylic fibers having a single fiber fineness of about 46 dtex were provided.

Comparative Example 1

Acrylic fibers having a single fiber fineness of about 46 dtex were provided in the same manner as Example 2 except that the fibers were washed in a water bath at 90° C. and the oil bath contained only oil.

Comparative Example 2

Preparation of Spinning Solution

Using the acrylic copolymer containing 46.0% of acrylonitrile, 52.0% of vinyl chloride, and 2.0% of sodium para-styrenesulfonate, which was obtained in Production Example 1, a spinning solution was prepared in the same manner as Example 1 except that the operating conditions of the thin film evaporator were set such that the number of revolutions was 380 rpm, the circumferential speed was 3.1 m/s, the centrifugal force per 100 mm axial length of a movable blade was 16.9 N, the pressure was 2.6 kPa, the inlet heating steam temperature was 130.2° C., and the outlet heating steam temperature was 129.6° C., and the amount of the slurry of the acrylic copolymer supplied to the thin film evaporator was 269.4 kg/hr·m². In this example, the centrifugal force per 100 mm axial length of a movable blade was 0.063 N with respect to the unit amount (1 kg/hr·m²) of the slurry of the acrylic copolymer supplied to the thin film evaporator. The thermal-centrifugal force efficiency index η was 219.2 N·cal/kg·° C. The spinning solution thus prepared contained the acrylic copolymer with a solid concentration of 28.0%, 0.02135% of tripolyphosphoric acid, and 4.9% of water with respect to 100% of the spinning solution. The spinning solution contained 17.5 parts of water with respect to 100 parts of the acrylic copolymer.

Wet Spinning

Using the above spinning solution, wet spinning was performed in the same manner as Example 1 except that the fibers were washed in a water bath at 90° C. and the oil bath contained a mixture of 100 parts of oil and 1.0 part of ethylene carbonate. Thus, acrylic fibers having a single fiber fineness of about 46 dtex were provided.

Comparative Example 3

Acrylic fibers having a single fiber fineness of about 46 dtex were provided in the same manner as Comparative Example 2 except that the oil bath contained only oil.

Comparative Example 4

Acrylic fibers having a single fiber fineness of about 46 dtex were provided in the same manner as Example 2 except that the oil bath contained a mixture of 100 parts by weight of oil and 1.0 part by weight of acetyl tributyl citrate (ATBC).

Comparative Example 5

Acrylic fibers having a single fiber fineness of about 46 dtex were provided in the same manner as Example 2 except that 20 parts by weight of acetyl tributyl citrate (ATBC) was added to 100 parts by weight of the acrylic copolymer in preparing the spinning solution, and that the fibers were washed in a water bath at 90° C. and the oil bath contained only oil in the wet spinning.

The content of the organic solvent A in the acrylic fibers in Examples 1 to 3 and Comparative Examples 1 to 5 were measured and calculated as follows. The surface roughness, void fraction, and apparent glass transition temperature of the acrylic fibers in Examples 1 to 3 and Comparative Examples 1 to 5 were measured and calculated as follows. The curl setting properties with hot water and the hackling properties of the acrylic fibers in Examples 1 to 3 and Comparative Examples 1 to 5 were evaluated as follows. Tables 1 and 2 show the results.

Content of Organic Solvent a in Acrylic Fibers

A glass sample bottle containing pure water was prepared, in which fibers were placed so that the water would not overflow. Then, the fibers were heated in hot water at 95° C. or more for 2 hours or more to extract the organic solvent in the fibers. The extract was analyzed by gas chromatography, and the mass (W1) of the organic solvent in the fibers was calculated. If two or more types of organic solvents A were contained in the fibers, the mass (W1) of each of the organic solvents A was calculated. The fibers in the glass sample bottle were washed with pure water, and then dried in an atmosphere at 110° C. for 4 hours or more. Thus, the mass (W2) of the dried fibers was measured. Using the following formula, the content of the organic solvent A in the acrylic fibers was calculated.

Content of organic solvent $A$ in acrylic fiber (% by mass)=$(W1)/(W1+W2) \times 100$ Surface Roughness The side surface of the fibers was observed by an ultra-deep color 3D profile measuring microscope ("VK-9500" series, manufactured by KEYENCE CORPORATION) at a magnification of 3000× (objective lens: 150×, integrated lens: 20). Then, an area of 40 μm long and 80 μm wide was arbitrarily selected from the observed image, and the surface area of the area of 40 μm long and 80 μm wide was measured using image analysis software VK Analyzer ("VK-H1XA" series, manufactured by KEYENCE CORPORATION). The average value, the maximum value, and the minimum value were measured to determine an average surface roughness, a maximum surface roughness, and a minimum surface roughness, respectively, where n=6.

Void Fraction

The cross section of a fiber bundle with a total fineness of about 14000 dtex was observed by an ultra-deep color 3D profile measuring microscope ("VK-9500" series, manufactured by KEYENCE CORPORATION) at a magnification of 400× (objective lens: 20×, integrated lens: 20×). Then, an area including about 70 filaments was arbitrarily selected from the observed image, and the total number of cross sections of the filaments and the number of cross sections of the filaments having a void (with a diameter of 2 μm or more) in this area were measured. The void fraction was calculated by the following formula. The diameter of a void was calculated by converting the area of the void to the area of a perfect circle.

Void fraction (%)=(Number of cross sections of filaments having void/Total number of cross sections of filaments)×100

Peak Temperature of tan δ

Using a thermal analysis measuring device (model "SSC/5200" manufactured by Seiko Instruments Inc.), a loss modulus (E") and a storage modulus (E') of the fibers were measured in accordance with JIS K 7244 under the conditions of a frequency of 0.05 Hz, a load of 25 mN±10 mN, and a temperature rise rate of 5° C./min. Then, the dynamic viscoelasticity (tan δ) was calculated by the following formula, and a temperature at which the dynamic viscoelasticity (tan δ) reached the maximum value was defined as a peak temperature of tan δ (apparent glass transition temperature).

Dynamic viscoelasticity (tan δ)=Loss modulus ($E''$)/Storage modulus ($E'$)

(Curl Setting Properties with Hot Water)

Acrylic fibers (total fineness: 7400 dtex) were cut to a length of 27 cm, and the resulting fiber bundle was wound around a 15 mm diameter pipe and fixed. This fiber bundle was immersed in hot water at 70° C. for 15 seconds, and then dried by ventilation drying at room temperature. Subsequently, the fiber bundle was removed from the pipe, and the length of the fiber bundle immediately after removal from the pipe was measured and evaluated in accordance with the following criteria. The curl setting properties with hot water (HWS properties) were improved as the length of the fiber bundle became shorter.

Good: The length of the fiber bundle immediately after removal from the pipe is 15.5 cm or less.

Poor: The length of the fiber bundle immediately after removal from the pipe is more than 15.5 cm.

Hackling Properties

After the fibers were crimped by a gear crimping machine, the fibers (total fineness: 1129000 dtex) were cut to a fiber length of 2 m. Holding near the middle of the cut fibers, the fibers were hackled by drawing them through a hackling board (i.e., a base studded with 1470 spikes, which was 66 cm wide and 120 cm long), and the resistance that would be felt when the fibers were pulled out of the hackling board was sensory evaluated in accordance with the following criteria.

Good: The resistance is small.

Poor: There is some resistance.

TABLE 1

| | Type of organic solvent A | Content of organic solvent A (% by mass) | Surface roughness (μm²) | | | Void fraction (%) | Apparent glass transition temperature (° C.) |
|---|---|---|---|---|---|---|---|
| | | | Average | Max | Min | | |
| Ex. 1 | DMSO dimethyl sulfone | 0.3 0.42 | 5582 | 6750 | 4465 | 31.0 | 86.9 |

TABLE 1-continued

| | Type of organic solvent A | Content of organic solvent A (% by mass) | Surface roughness ($\mu m^2$) Average | Max | Min | Void fraction (%) | Apparent glass transition temperature (°C) |
|---|---|---|---|---|---|---|---|
| Ex. 2 | DMSO dimethyl sulfone | 0.3 0.42 | 5171 | 6163 | 4403 | 44.7 | 86.9 |
| Ex. 3 | DMSO ethylene carbonate | 0.03 0.36 | 5582 | 6750 | 4465 | 31.0 | 87.0 |
| Comp. Ex. 1 | DMSO | 0.09 | 5171 | 6163 | 4403 | 44.7 | 86.9 |
| Comp. Ex. 2 | DMSO ethylene carbonate | 0.03 0.36 | 5957 | 6879 | 5193 | 21.5 | 87.0 |
| Comp. Ex. 3 | DMSO | 0.09 | 5957 | 6879 | 5193 | 21.5 | 95.9 |
| Comp. Ex. 4 | DMSO ATBC | 0.01 detection limit or less | 5011 | 6029 | 4320 | 44.7 | 96.1 |
| Comp. Ex. 5 | DMSO | 0.02 | 6221 | 7340 | 5220 | 89.0 | 93.2 |

TABLE 2

| | Curl setting properties with hot water | | Hackling properties |
|---|---|---|---|
| | Fiber length (cm) | Evaluation | |
| Ex. 1 | 13.7 | good | good |
| Ex. 2 | 13.7 | good | good |
| Ex. 3 | 13.5 | good | good |
| Comp. Ex. 1 | 16.1 | poor | good |
| Comp. Ex. 2 | 13.5 | good | poor |
| Comp. Ex. 3 | 16.1 | poor | poor |
| Comp. Ex. 4 | 15.9 | poor | good |
| Comp. Ex. 5 | 16.2 | poor | poor |

As can be seen from the results of Tables 1 and 2, the acrylic fibers in Examples 1 to 3, in which the content of the organic solvent A in the acrylic fibers was 0.1 to 3% by mass and the average surface roughness was 5900 $\mu m^2$ or less in the area of 40 $\mu m$ long and 80 $\mu m$ wide of the side surface of the fibers, had good curl setting properties with hot water and good hackling properties.

The acrylic fibers in Comparative Example 1 had poor curl setting properties with hot water because the content of the organic solvent A in the acrylic fibers was less than 0.1% by mass. The acrylic fibers in Comparative Example 2 had poor hackling properties because the average surface roughness was more than 5900 $\mu m^2$ in the area of 40 $\mu m$ long and 80 $\mu m$ wide of the side surface of the fibers. The acrylic fibers in Comparative Example 3 had poor curl setting properties with hot water and poor hackling properties because the content of the organic solvent A in the acrylic fibers was less than 0.1% by mass, and the average surface roughness was more than 5900 $\mu m^2$ in the area of 40 $\mu m$ long and 80 $\mu m$ wide of the side surface of the fibers. In the fibers in Comparative Example 4, the oil was applied along with ATBC which was generally used as a plasticizer for a vinyl chloride resin. In the fibers in Comparative Example 5, ATBC was added to the spinning solution (the content of ATBC in the fibers was 5.2% by mass). Both the fibers in Comparative Examples 4 and 5 had poor curl setting properties with hot water. Moreover, the fibers in Comparative Example 5 also had poor hackling properties.

DESCRIPTION OF REFERENCE NUMERALS

1 Production apparatus for spinning solution
10 Feed tank
11 Liquid feed pump
12, 29, 31, 41 Conduit
20 Thin film evaporator (having movable blade)
21 Feed inlet
22, 700, 800 Heat transfer body
23, 723, 823 Jacket
24 Motor
25, 125 Rotation axis
26, 26a to 26h, 126, 226, 326, 726, 826 Movable blade
27 Vaporized component outlet
28 Bottom outlet
30 Condenser
40 Bottom recovery tank
50 Condensate recovery tank
60 Vacuum pump
110 Agitator
210 Blade support ring
211 Support ring fixture
220, 320 Movable blade holder
230 Mechanical seal
240 Upper bearing
250 Lower bearing
300 Acrylic fiber
400 Contact portion between fiber bundle and nip roll
500 Nip roll
501 Upper nip roll
502 Lower nip roll
600 Cylinder
610 Inner tube of cylinder
701, 703 Portion where no thin film is formed
702, 802 Thin film formation and evaporation portion
801, 803 Unheated portion
900 Inner wall surface of heat transfer body Although the disclosure has been described with respect to only a limited number of embodiments, those skilled in the art, having benefit of this disclosure, will appreciate that various other embodiments may be devised without departing from the scope of the present invention. Accordingly, the scope of the present invention should be limited only by the attached claims.

What is claimed is:

1. A method for producing an acrylic fiber for artificial hair, the method comprising:
    preparing a spinning solution by dissolving an acrylic copolymer obtained by copolymerizing acrylonitrile, vinyl chloride, and a sulfonic acid group-containing vinyl monomer in an organic solvent; and
    wet spinning the spinning solution to form an acrylic fiber, wherein:
        the spinning solution comprises 8 to 16 parts by mass of water with respect to 100 parts by mass of the acrylic copolymer,
        in the wet spinning, a content of the organic solvent in the acrylic fiber is adjusted to 0.1 to 3% by mass,
        the wet spinning comprises at least a water washing process and an oil application process,
        in the oil application process, a water-washed acrylic fiber is impregnated with an organic solvent that can dissolve the acrylic copolymer while the oil is applied to the water-washed acrylic fiber, and
        the organic solvent used in preparing the spinning solution comprises dimethyl sulfoxide, and the organic solvent impregnated into the acrylic fiber in the oil application process comprises at least one selected from the group consisting of dimethyl sulfone, ε-caprolactam, and sulfolane.

2. The method according to claim 1, wherein the water washing process is performed by spraying water on the acrylic fiber and pressing the acrylic fiber sprayed with water by a nip roll.

3. The method according to claim 1, the method further comprising preparing the acrylic copolymer by an emulsion polymerization method, wherein
    the acrylonitrile, the vinyl chloride, and the sulfonic acid group-containing vinyl monomer are continuously polymerized in a single reaction vessel,
    the sulfonic acid group-containing vinyl monomer is not introduced into the reaction vessel at the beginning of a polymerization reaction, and
    the sulfonic acid group-containing vinyl monomer is continuously introduced into the single reaction vessel at a constant rate during a period from when a yield of the acrylic copolymer reaches 8 to 21% by mass of an intended amount of the acrylic copolymer until when the polymerization reaction ends.

4. The method according to claim 1, wherein preparing the spinning solution comprises:
    forming a slurry of the acrylic copolymer comprising the acrylic copolymer, water, and the organic solvent; and
    evaporating the water in the slurry after supplying the slurry to a thin film evaporator.

5. The method according to claim 1, wherein the spinning solution further comprises a polyphosphate.

6. The method according to claim 1, wherein the acrylic copolymer comprises 30 to 70% by mass of the acrylonitrile, 25 to 69.5% by mass of the vinyl chloride, and 0.5 to 5% by mass of the sulfonic acid group-containing vinyl monomer, with respect to a total mass of the acrylic copolymer.

7. The method according to claim 3, wherein the acrylic copolymer comprises 30 to 70% by mass of the acrylonitrile, 25 to 69.5% by mass of the vinyl chloride, and 0.5 to 5% by mass of the sulfonic acid group-containing vinyl monomer, with respect to a total mass of the acrylic copolymer.

8. The method according to claim 5, wherein the polyphosphate is an inorganic polyphosphate.

* * * * *

UNITED STATES PATENT AND TRADEMARK OFFICE
CERTIFICATE OF CORRECTION

PATENT NO. : 12,031,239 B2
APPLICATION NO. : 17/152916
DATED : July 9, 2024
INVENTOR(S) : Satoru Yoshimura et al.

Page 1 of 1

It is certified that error appears in the above-identified patent and that said Letters Patent is hereby corrected as shown below:

On the Title Page

Add item (30):
(30) Foreign Application Priority Data
Japanese Patent Application
No. 2015-130233 filed on June 29, 2015.

Signed and Sealed this
Nineteenth Day of November, 2024

Katherine Kelly Vidal
*Director of the United States Patent and Trademark Office*